United States Patent
Mio et al.

(10) Patent No.: US 11,833,109 B2
(45) Date of Patent: Dec. 5, 2023

(54) PACKAGE (71) Applicant: Fujimori Kogyo Co., Ltd., Tokyo (JP)

(72) Inventors: Atsushi Mio, Yokohama (JP); Toyoaki Suzuki, Yokohama (JP); Junpei Nomura, Yokohama (JP); Kaho Toyabe, Yokohama (JP); Hajime Okamoto, Yokohama (JP)

(73) Assignee: Fujimori Kogyo Co., Ltd.

( * ) Notice: Subject to any disclaimer, the term of this patent is extended or adjusted under 35 U.S.C. 154(b) by 0 days.

(21) Appl. No.: 16/770,348

(22) PCT Filed: Dec. 5, 2018

(86) PCT No.: PCT/JP2018/044701
§ 371 (c)(1),
(2) Date: Jun. 5, 2020

(87) PCT Pub. No.: WO2019/111940
PCT Pub. Date: Jun. 13, 2019

(65) Prior Publication Data
US 2020/0383869 A1   Dec. 10, 2020

(30) Foreign Application Priority Data
Dec. 8, 2017   (JP) .................................. 2017-236530

(51) Int. Cl.
*A61J 1/10*   (2006.01)
*A61J 1/14*   (2023.01)
(Continued)

(52) U.S. Cl.
CPC .............. *A61J 1/10* (2013.01); *A61J 1/1468* (2015.05); *B32B 1/00* (2013.01); *B32B 7/12* (2013.01);
(Continued)

(58) Field of Classification Search
CPC .......... A61J 1/10; A61J 1/1468; A61J 1/1475; A61J 1/12; A61J 1/1412; A61M 5/148;
(Continued)

(56) References Cited

U.S. PATENT DOCUMENTS

| 5,928,201 A | 7/1999 | Poulsen |
| 6,340,357 B1 | 1/2002 | Poulsen et al. |

(Continued)

FOREIGN PATENT DOCUMENTS

| CN | 101238046 A | 8/2008 |
| CN | 101478945 A | 7/2009 |

(Continued)

OTHER PUBLICATIONS

International Search Report for PCT/JP2018/044701 dated Feb. 19, 2019 (2 pages).

(Continued)

*Primary Examiner* — James C Yager
(74) *Attorney, Agent, or Firm* — ST. ONGE STEWARD JOHNSTON & REENS LLC (57) ABSTRACT

A package has a bag body, at least one mouth part member bonded to the bag body, and a contained product being a liquid housed in the bag body. The bag body is formed in a bag shape by using laminates each having a sealant layer and a water vapor barrier layer composed at least of a fluorine-based resin, and by bonding together the sealant layers opposing each other so that the sealant layers are to be located on the inside of the bag body. The mouth part member is sandwiched between the oppositely facing sealant layers and is bonded thereto. The volume V of the contained product housed in the bag body is 0.1-20 cm$^3$, and the relation between the area S (cm$^2$) where the bag body is (Continued)

in contact with the contained product housed in the bag body and the aforementioned volume V (cm$^3$) satisfies $0.05 \leq V/S \leq 0.25$ (formula (I)).

8 Claims, 2 Drawing Sheets

(51) Int. Cl.
- *B32B 1/00* (2006.01)
- *B32B 7/12* (2006.01)
- *B32B 27/08* (2006.01)
- *B32B 27/32* (2006.01)

(52) U.S. Cl.
CPC ............ *B32B 27/08* (2013.01); *B32B 27/322* (2013.01); *B32B 27/325* (2013.01); *A61J 1/1475* (2013.01); *B32B 2250/242* (2013.01); *B32B 2307/7246* (2013.01); *B32B 2439/46* (2013.01); *B32B 2439/80* (2013.01); *Y10T 428/1334* (2015.01); *Y10T 428/1341* (2015.01); *Y10T 428/1352* (2015.01); *Y10T 428/1379* (2015.01)

(58) Field of Classification Search
CPC .. B32B 1/00; B32B 7/12; B32B 27/08; B32B 27/322; B32B 27/325; B32B 2250/242; B32B 2307/7246; B32B 2439/46; B32B 2439/80; B32B 27/304; B32B 27/32; Y10T 428/1334; Y10T 428/1341; Y10T 428/1352; Y10T 428/1379
See application file for complete search history.

(56) References Cited

U.S. PATENT DOCUMENTS

| | | | |
|---|---|---|---|
| 6,572,603 | B1 | 6/2003 | Tani |
| 2003/0008152 | A1 | 1/2003 | Tsai |
| 2004/0001655 | A1* | 1/2004 | Proicou ............... A61J 1/1406 383/202 |
| 2004/0188281 | A1 | 9/2004 | Iwasa |
| 2008/0063825 | A1* | 3/2008 | Mori ..................... A61J 1/10 428/347 |
| 2017/0202740 | A1 | 7/2017 | Yoshida et al. |

FOREIGN PATENT DOCUMENTS

| | | |
|---|---|---|
| CN | 107428144 A | 12/2017 |
| DE | 19537271 A1 | 4/1997 |
| EP | 2229927 A1 | 9/2013 |
| JP | 57059553 A | 4/1982 |
| JP | 03124578 A | 5/1991 |
| JP | H06083725 B2 | 10/1994 |
| JP | H06296688 A | 10/1994 |
| JP | 11236063 A | 8/1999 |
| JP | 2004501799 A | 1/2004 |
| JP | 2004050601 A | 2/2004 |
| JP | 2004160823 A | 6/2004 |
| JP | 2004276966 A | 10/2004 |
| JP | 2005145492 A | 6/2005 |
| JP | 2008143582 A | 6/2008 |
| JP | 2010081971 A | 4/2010 |
| JP | H2014057723 A | 4/2014 |
| JP | 2014171571 A | 9/2014 |
| JP | 2015074471 A | 4/2015 |
| JP | 2016222324 A | 12/2016 |
| JP | 2017077894 A | 4/2017 |
| KR | 1020040111618 A | 12/2004 |
| KR | 1020090110853 A | 10/2009 |
| WO | 99039679 A1 | 8/1999 |
| WO | 0200435 A1 | 1/2002 |
| WO | 03068135 A1 | 8/2003 |

OTHER PUBLICATIONS

European Search Report for EP Application No. 18885808.8; dated Feb. 8, 2021; 7 pages.
European Patent Office Third Party Observation for Application No. 18885808.8 dated Dec. 21, 2022.
Jinjian Yang et al., "Prediction of a shelf-life of cheerios by a nonlinear isothermal adsorption line", Food and Fermentation Industries No. 2, pp. 15-18, Feb. 29, 1996.
National Intellectual Property Administration, PRC Office Action for Application #201880078413.8 dated Oct. 12, 2022.
National Intellectual Property Administration, PRC Office Action in Application No. 201880078413.8 dated Mar. 12, 2023.
Japan Patent Office Notice of Reasons for Cancellation for Application No. 2019-558246 dated Sep. 22, 2023
Decision to Grant from Kroean Intellectual Property Office for Application No. 10-2020-7017463 dated Sep. 25, 2023 (with translation).

* cited by examiner

PACKAGE

FIELD OF THE INVENTION

The present invention relates to a package which accommodates liquid contents such as pharmaceutical products and the like which are administered epidurally and subcutaneously, and are administered to arteriovenous blood vessels, muscle, various organs, and the like; which is compact, lightweight, and portable; and in which the quality of the pharmaceutical products is unlikely to change, and the amount of residual drug is small after administration.

BACKGROUND OF THE INVENTION

For continuous administration of hormones, narcotics for relieving pain, anticancer drugs, or antibiotics, it is common to perform a method of injecting these drug solutions subcutaneously and epidurally and into blood vessels, muscle, various organs, and the like by a micropump. In this case, administration can be controlled by an electric circuit or a computer, and a small amount of administration or finely controlled administration according to conditions of a patient is performed.

A pump mechanism that enables such a drug solution injection system to be portable has also been developed. For the pump mechanism, for example, a type in which a syringe filled with a drug solution is pressure-driven by a battery, a peristaltic pump that uses an electric motor as a power source, and the like are known. With recent technological innovations, the reliability and durability of the devices themselves have improved dramatically, and a micropump-type portable medical pump device is becoming widespread (that is, a portable device for continuous drug administration, hereinafter may be referred to as a "pump device").

These pump devices alleviate the burden of frequent administration by pen-type injections and the like which are performed by patients themselves, and this is expected to lead to an improvement in quality of life (QOL) as compared with those of the related art.

When using such a pump device described above, it is necessary to perform an operation of replenishing a storage part (reservoir) with a drug. A drug solution for injection needs to be injected into a human body without being mixed with air. Accordingly, such a pump device described above is used after expelling air by putting a drug solution into a container for injection.

For example, in continuous administration of insulin using a "MiniMed 620G" system manufactured by Medtronic, it is necessary to perform a preparatory operation in which an insulin preparation stored in a glass vial container is injected into an empty syringe-like reservoir that has been sterilized in advance, and thereafter, bubbles are manually expelled.

The injection of a drug solution into a reservoir and the preparatory operation are extremely complicated and difficult to perform. The detailed procedure is shown by open sources such as drawings and videos on the Internet, but because the preparatory operation for injection of drug solutions is performed in general living environments, there is a problem of accompanying risks of contamination due to incorporation of bacteria, dust, and the like, and this is not preferable. In addition, it is also desirable to avoid such an operation from the viewpoint of a high risk of exposure of operators in a case where a highly pharmacologically active substance such as an anticancer drug is contained as a component of a pharmaceutical product.

Meanwhile, a type of drug solution injection device in which a device or a reservoir of a prefilled type in which a drug solution is sealed in advance is replaced has been proposed. For example, as disclosed in Japanese Unexamined Patent Application, First Publication No. H6-83725 and Japanese Unexamined Patent Application, First Publication No. H6-296688, there is a type in which a balloon made of an elastic material is filled with a drug solution, and the drug solution is injected using a contractile force of the balloon.

In a case of using the pressure of a drug solution container such as balloon pressure or gas pressure, it is possible to configure a drug solution injection device which is compact, lightweight, and inexpensive, and which is easily operated as compared to the above-described case of using an electric pump such as a syringe pump or peristaltic pump. In addition, when an orifice (a fluid resistor having fine holes) at an outlet of a container is adjusted, continuous injection in small amounts is possible. However, because the ejection pressure which is the balloon pressure or the gas pressure cannot be arbitrarily adjusted, and a flow rate is adjusted with a single orifice, only one flow rate setting is possible for one drug solution injection device.

Furthermore, because a flow path cannot be turned on and off arbitrarily and automatically, continuous injection operates only at a flow rate that is initially set. Accordingly, it is difficult to appropriately control a drug solution administration method by increasing or decreasing a flow rate according to daily activities, setting an administration interval, and the like.

In recent years, a type has been put into practical use, in which replenishing with a drug solution is easily performed by replacing a drug solution storage part connected to a pump device with a prefilled type cartridge. For example, U.S. Pat. No. 6,340,357 proposes a type in which a syringe-type prefilled cartridge is attached inside an administration device, a gasket inside the cartridge is moved such that a rod is moved forward by an electric motor installed in the device, and thereby a set dose of a drug solution is administered.

A prefilled cartridge used in such a type requires to have a stroke equivalent to a plunger of a syringe to administer the entire amount of a drug solution, and therefore there is a limitation in reducing the size of a pump device. Alternatively, in a case of attempting to reduce the size of a pump device, there is a problem of a filling amount of a drug solution becoming small. It has been pointed out that an increase in pump device size leads to a decrease in portability, which is a problem from the viewpoint of necessity of continuous administration.

It is effective to use a flexible pouch type reservoir for reducing the size of a pump device. For example, FIG. 8 of Japanese Unexamined Patent Application, First Publication No. 2014-171571 shows a mode in which a drug solution is accommodated in a space formed by a cartridge base and a flexible reservoir film. The reservoir film is deformed as the drug solution is discharged by a micropump, and thereby the amount of residual drug solution can be minimized. It is described that the reservoir film is preferably processed to have a curved surface so that the film comes into close contact with the cartridge base as the amount of a drug solution decreases.

However, since the reservoir film is subjected to curved surface processing in this type, a material of the film needs to be thermoformable, which is regarded as a problem. In addition, when the cartridge base and the reservoir film are not precisely aligned, the amount of residual liquid increases, which is regarded as a problem. Due to these problems, this type is not preferable from the viewpoint of productivity and manufacturing cost. Furthermore, when the reservoir film is made thin to facilitate its deformation, water vapor barrier properties are degraded, and the concentration of a drug solution is likely to change, which is regarded as another problem.

In particular, because a volume of a container used for continuous infusion of insulin is 1.5 mL to 3 mL, which is an extremely small volume, even a small amount of residual liquid cannot be ignored in such a container, and at the same time, even a slight evaporation of moisture causes significant change in concentration of a drug solution. Therefore, barrier properties and flexibility are required to be compatible to achieve maintenance of the concentration of a drug solution.

SUMMARY OF THE INVENTION

As described above, pump devices of the related art and reservoirs thereof are effective for a treatment by continuous administration of a drug solution, but there are many restrictions in manufacturing and operation, and the spread thereof has been limited.

The present invention has been made in view of the above circumstances, and an object thereof is to provide a package which is compact, lightweight, and portable, and in which a reservoir of a pump device does not have a complicated structure or material, the quality of contents is unlikely to change, and the amount of residual contents after administration is small.

The inventors of the present application have completed the following inventions to achieve the above-mentioned object.

To achieve the above-mentioned object, the present invention provides:
a package including a bag main body; at least one mouth part member joined to the bag main body; and a liquid content accommodated in the bag main body,
in which the bag main body of the package has, as a forming material, a laminate having at least a water vapor barrier layer made of a fluorine resin and a sealant layer, and is formed into a bag shape by bonding sealant layers facing each other, where the sealant layers are on an inner side,
the mouth part member is joined to the bag main body by being sandwiched between the sealant layers facing each other,
a volume V of the content accommodated inside the bag main body is 0.1 to 20 (cm$^3$), and
a relationship between an area S (cm$^2$) of the bag main body which comes into contact with the liquid content accommodated inside the bag main body and the volume V (cm$^3$) satisfies (Formula I).

$$0.05 \leq V/S \leq 0.25 \quad \text{(Formula I)}$$

In the package, the content accommodated in the package may be discharged through the mouth part member of the package, and a volume of the bag main body may be reduced according to the discharge of the content.

A water vapor permeation rate of the package may be 0.02% to 0.19%.

A thickness of the water vapor barrier layer may be within a range of 5 μm to 50 μm. The total thickness of the laminate may be within a range of 15 μm to 200 μm. The fluorine resin may be polychlorotrifluoroethylene.

The sealant layer may be composed of one or more layers and may include a layer formed of a cyclic olefin resin as a main component. The mouth part member may contain a cyclic olefin resin as a forming material.

The content may be a pharmaceutical product. The pharmaceutical product may be an injection. The injection may contain one or more selected from hormones, medical narcotics, local anesthetics, analgesics, anticancer drugs, and antibiotics as components.

Advantageous Effects of Invention

According to the package of the present invention, in a case where a mouth part member is connected to a pump device and a micropump is operated, a bag main body is deformed according to a negative pressure inside a reservoir, and contents are stably discharged without applying an excessive load to the micropump. In addition, due to a high level of water vapor barrier properties of the package, evaporation of moisture is less likely to occur, and the concentration of a drug solution is kept constant even during long-term storage before start of administration. Furthermore, the amount of residual contents is extremely small after completion of administration. For example, even in a case where an expensive drug is sealed in as a content, disposal loss is reduced. Accordingly, the package also has an effect of being simply and easily handled from the viewpoint of manufacturing a container and filling the container with contents.

DETAILED DESCRIPTION OF THE INVENTION

Hereinafter, preferable embodiments of the present invention will be described in detail with reference to the drawings.

Figure 1:
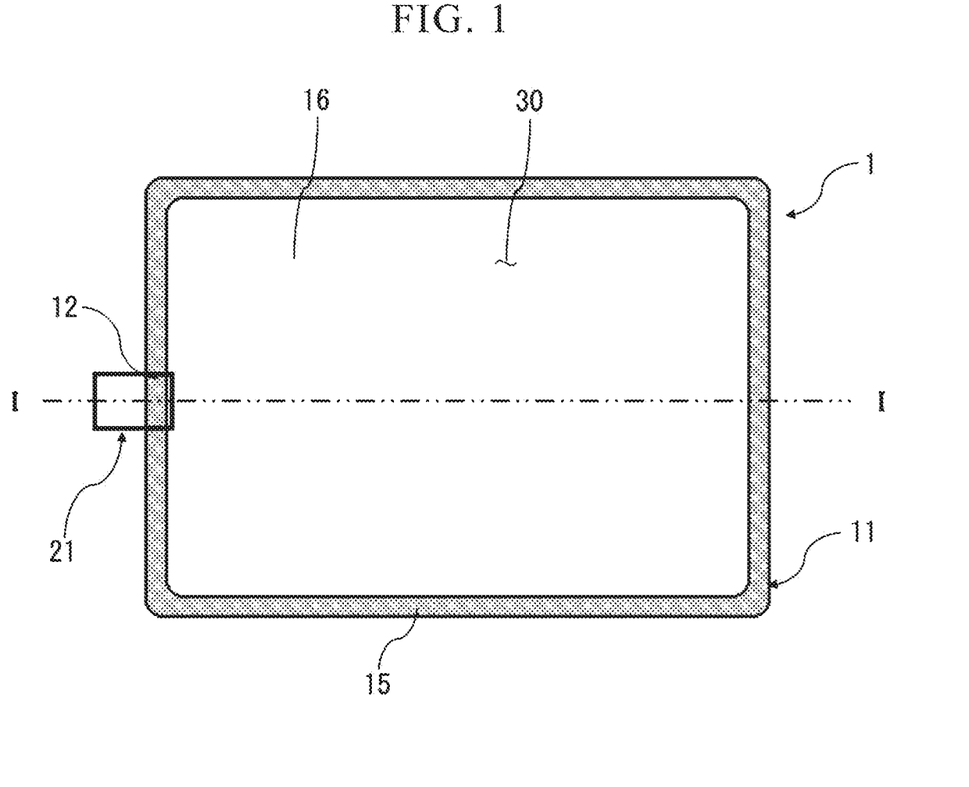
FIG. 1 is a front view of a package representing a typical embodiment of the present invention.

FIG. 1 is a front view showing a package according to one embodiment of the present invention. A package 1 includes a bag main body 11 serving as a storage part for a content 16, and a mouth part member 21.

Figure 2:
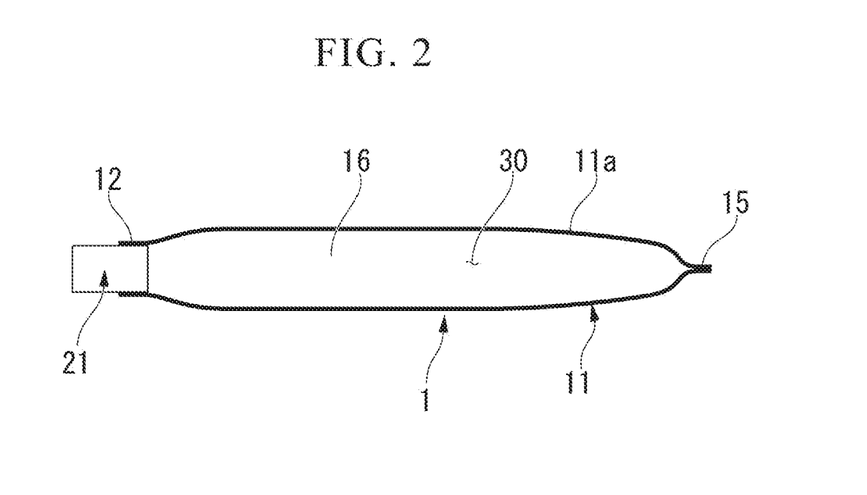
FIG. 2 is a partial cross-sectional view of the package of the present invention.

FIG. 2 shows a cross section taken along a line I-I of FIG. 1 of the package 1 in a state where the content 16 is accommodated. In the following description, explanation will be made with the mouth part member 21 in a state of being oriented to the left for easy understanding, but the package of the present invention may be used in any posture without being fixed in this orientation.

The package 1 includes the rectangular bag main body 11 having an accommodation part 30 capable of accommodating the content 16 therein, and the cylindrical mouth part member 21 inserted into and joined to an opening part 12 formed at the center of one end of the bag main body 11. In the bag main body 11, outer peripheral portions of two rectangular laminates 4 made of resin are bonded or heat-sealed to be joined to each other. A seal part 15 is formed over the entire circumference except the opening part 12, and the accommodation part 30 is formed inside the seal part.

A shape of the bag main body 11 is not limited to the illustrated shape, and the bag main body 11 may have any shape as long as it has a bag shape. For example, the bag main body 11 may have a shape in which one laminate 4 is folded in two and the other parts are joined using a center folding line as the bottom of the bag main body 11. Alternatively, the bag main body 11 may have a shape in which the laminate 4 is rolled into a tubular shape such that both ends and bonding surfaces are joined together. Furthermore, a seal shape does not have to be a combination of straight lines, and may be a combination of arc-shaped sides, for example. The bag main body 11 may be formed into a three-dimensional box shape using the laminate 4. Even in a case where the bag main body 11 is formed in a box shape or a cylinder shape, it can maintain flexibility.

The size of the bag main body 11 is not limited in the present invention, but when a length in a major axis direction is 20 to 100 mm, a width in a minor axis direction is 10 to 100 mm, and a filling amount of the content 16 is about 1 to 100 $cm^3$, it is suitable as a package for pharmaceutical products and the like.

A volume of the bag main body 11 appropriately decreases as the amount of the content 16 decreases, but because a supply rate of the content 16 needs to be kept constant, the bag main body 11 preferably has a high degree of flexibility within a range not causing problems in manufacturing and use thereof, for example. For this reason, a tensile elastic modulus of the laminate 4 constituting the bag main body 11 is not limited, but it is preferably 1,500 MPa or less and more preferably 200 to 1,200 MPa. A thickness of the laminate 4 is not limited, but it is preferably 30 to 200 µm and more preferably 40 to 100 µm. When a tensile elastic modulus is too small, or a thickness of the laminate 4 is too small, the laminate 4 is easily stretched during manufacture of the package, which makes production difficult. When a tensile elastic modulus is excessively large or a thickness of the laminate 4 is excessively large, the bag main body 11 is inflexible, and a proportion of the laminate 4 occupying a volume in the pump device increases. Thereby, a volume for accommodation by the accommodation part 30 decreases. A tensile elastic modulus of the laminate can be measured by a measurement method specified in ISO 527-1.

The laminate 4 of the present embodiment is highly flexible, and therefore the bag main body 11 can be easily deformed when the content 16 is discharged, the load of a micropump that operates to remove the content 16 is reduced, and conformability is favorable in a case where an administration rate is constant or an administration rate is changed by program control.

Figure 3:
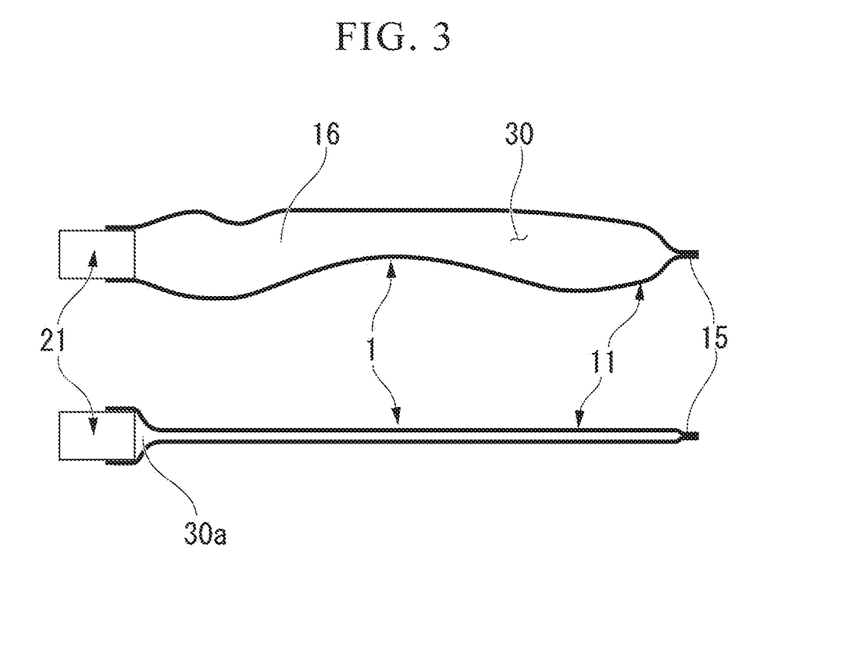
FIG. 3 is a partial cross-sectional view of the present invention for explaining deformation of the package.

FIG. 3 schematically shows a shape change of the bag main body 11 when the pump device is connected to discharge the content 16. A volume of the bag main body 11 gradually decreases as the content 16 is discharged, and thereby it is possible to minimize a space 30a after the discharge which is generated inside the bag main body 11 when the entire amount is discharged. In a case where the laminate 4 used for the bag main body 11 is not flexible, it becomes difficult to deform the bag main body 11 according to discharge, and the amount of residual content around the mouth part increases when the discharge of the content 16 is completed. According to the package 1 of the present invention, since the space 30a after discharge is small, disposal loss is reduced particularly when expensive contents are accommodated, and this is advantageous in terms of cost.

Laminate

Figure 4:
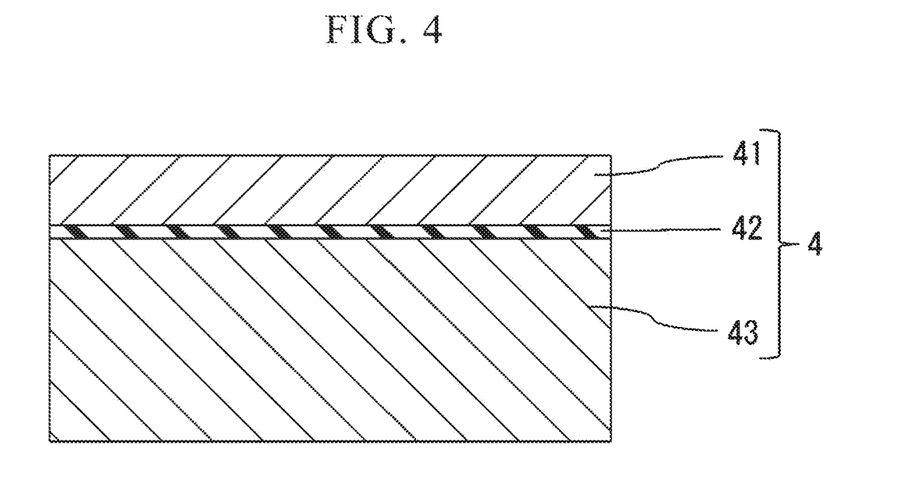
FIG. 4 is a cross-sectional view of a laminate constituting the package representing the present invention.

The laminate 4 constituting the bag main body 11 may be configured to have a water vapor barrier layer 41, an interlayer 42, and a sealant layer 43 in this order, which are illustrated in FIG. 4. The bag main body 11 shown in FIG. 1 is configured such that, using two laminates 4, sealant layers 43 of each of the laminates 4 are made to face each other and bonded to each other to serve as a seal part. For the laminate 4 constituting the package 1 of the present invention, materials to be described later are appropriately selected according to characteristics and purposes of the package 1 and the content 16 and the materials are laminated on each other by an extrusion laminating method, a dry laminating method, a multilayer co-extrusion film formation method, and the like.

Water Vapor Barrier Layer

The water vapor barrier layer 41 is a layer disposed to prevent alteration of the content 16 accommodated in the bag main body 11. The water vapor barrier layer 41 of the present embodiment includes a layer having a fluorine resin as a forming material. When the water vapor barrier layer 41 has a layer containing a fluorine resin as a forming material, it is possible to provide a laminate having excellent mechanical strength and optical properties and low water vapor permeability, and to provide a package formed from the same.

As the fluorine resin, it is possible to use polytetrafluoroethylene (PTFE), tetrafluoroethylene/perfluoroalkyl vinyl ether copolymer (PFA), tetrafluoroethylene/hexafluoropropylene copolymer (FEP), tetrafluoroethylene/hexafluoropropylene/perfluoroalkyl vinyl ether (EPA), tetrafluoroethylene/ethylene copolymer (ETFE), polyvinylidene fluoride (PVDF), polychlorotrifluoroethylene (PCTFE), chlorotrifluoroethylene/ethylene copolymer (ECTFE), and one or a mixture of two or more kinds of these. Among them, polychlorotrifluoroethylene (PCTFE), which has a high level of water vapor barrier properties and excellent flexibility, is preferable.

It is known that a fluorine resin has a higher glass transition temperature than a resin such as polyethylene terephthalate (PET) used as a base layer of the vapor-deposited polyester film which has been applied to the water vapor barrier layer 41 in the package material. For this reason, as a material for forming the sealant layer 43, it is possible to apply a material that could not be applied because a glass transition temperature was too high in the related art, and it is possible to widen the choice of materials forming the sealant layer 43.

The water vapor barrier layer 41 may have a single-layer structure composed of one layer or a laminated structure of two or more layers. It may further have a layer having gas barrier properties or functions other than gas barrier properties (hereinafter referred to as "other layer"). Examples of other layers include a reinforcement layer, a gas barrier layer, a light-shielding layer, a printing layer, a metal foil, a synthetic paper, and the like. The other layers may be configured not to contain a fluorine resin.

The laminate 4 may have a printing layer or a coat layer on the surface opposite to the sealant layer. The printing layer can impart distinguishing properties and design properties of the package 1 by printing ink on the surface of the water vapor barrier layer 41. The coating layer may be a layer for protecting the water vapor barrier layer 41 or the printing layer provided on the water vapor barrier layer 41 or for improving gas barrier properties, and may be a coating layer formed using a thin resin layer or an ultraviolet-curable resin. Furthermore, resin layers and the like made of different materials may be provided outside the water vapor barrier layer 41.

In the present embodiment, a thickness of the layer containing a fluorine resin as a forming material is preferably 5 μm to 50 μm, and more preferably 15 μm to 25 μm. When a thickness of the layer containing a fluorine resin as a forming material is 15 μm or more, a water vapor permeation rate of the package 1 can be sufficiently lowered. In addition, when a thickness of the layer containing a fluorine resin as a forming material is 25 μm or less, production costs can be reduced, and flexibility for smoothly discharging the content 16 can be imparted.

Interlayer

The interlayer 42 improves adhesiveness between the water vapor barrier layer 41 and the sealant layer 43. In the package of the present invention, the interlayer 42 is not an essential layer and is a layer provided to obtain sufficient adhesiveness between layers based on a combination of the water vapor barrier layer 41 and the sealant layer 43 and a method for manufacturing a laminate. A material forming the interlayer 42 is not particularly limited as long as it can improve adhesiveness of these layers. For example, the interlayer 42 is preferably formed of a polyurethane-based adhesive, or a resin composition containing a polyethylene-based resin and a modified polyethylene-based resin which is a composition found by the inventors of the present application and already described in Japanese Patent Application No. 2017-091287.

By forming the interlayer 42 using the materials as described above, it is possible to provide the package 1 in which separation between the water vapor barrier layer 41 and the interlayer 42, or between the interlayer 42 and the sealant layer 43 does not easily occur. Furthermore, it is possible to inhibit delamination of the laminates and cracking of the package 1 by imparting more favorable adhesiveness to the interlayer 42.

Sealant Layer

The sealant layer 43 is used when the laminate 4 is laminated by heat sealing or the like to form a bag. The sealant layer 43 is a layer that comes into contact with the content 16 in the package 1 of the present invention.

As a material of the sealant layer 43, for example, it is possible to use polyethylene (PE), polypropylene (PP), ethylene-vinyl acetate copolymer (EVA), a polyolefin resin such as a cyclic olefin resin, a polyester resin, and the like, but examples are not limited to the above-mentioned materials.

The sealant layer 43 in the present embodiment does not need to use the above-mentioned resin materials alone, and may be obtained by disposing two or more kinds of materials in multiple layers or by blending different materials. By combining a plurality of materials, it is possible to enhance various physical properties necessary for maintaining the quality of the content 16, such as heat resistance, flexibility, transparency, impact resistance, and heat seal strength.

In the present embodiment, the water vapor barrier layer 41 has a layer having a high glass transition temperature and containing a fluorine resin as a forming material. Accordingly, the sealant layers 43 can be bonded to each other at high temperature using heat sealing or the like. Therefore, it is possible to select and use a material having a high glass transition temperature as a material for forming the sealant layer 43.

It is also known that as a glass transition temperature of the material forming the sealant layer 43 becomes higher, non-adsorption properties with respect to the content 16 becomes excellent. The sealant layer 43 of the present embodiment preferably contains a cyclic olefin resin. When the sealant layer 43 contains a cyclic olefin resin, it is possible to provide a package having excellent non-adsorption properties with respect to the content 16.

Examples of cyclic olefin resins include a cyclic olefin polymer (COP), a cyclic olefin copolymer (COC), and the like. A resin component constituting the sealant layer may be one or more kinds of cyclic olefin resins, or may be a mixture of cyclic olefin resin and other resin, elastomer, or the like.

Examples of COP include homopolymers of cyclic olefins, copolymers of two or more kinds of cyclic olefins, or hydrogenated products thereof. The cyclic olefin polymer is preferably a non-crystalline polymer, and more preferably a ring-opening polymer of cyclic olefin by metathesis or the like, or hydrogenated products thereof. The cyclic olefin polymer has a higher proportion of containing an alicyclic structure than that of the cyclic olefin copolymer and the like, and has excellent non-adsorption properties with respect to the content 16.

Examples of COC include a copolymer of one or more kinds of cyclic olefins and one or more kinds of non-cyclic olefins, or hydrogenated products thereof. The cyclic olefin copolymer is preferably a non-crystalline polymer, more preferably a copolymer of cyclic olefin and ethylene, or hydrogenated products thereof.

The cyclic olefin used as a constituent monomer of the cyclic olefin resin is an unsaturated hydrocarbon (olefin) having at least one ring structure. Examples thereof include vinyl cycloalkanes having cycloalkane having 3 to 20 carbon atoms and derivatives thereof, monocycloalkenes having 3 to 20 carbon atoms and derivatives thereof, cyclic olefins having a norbornene skeleton (norbornene-based monomers), and the like.

Examples of norbornene-based monomers include bicyclo[2.2.1]-2-heptene (norbornene) and its derivatives. Examples of derivatives include a compound having a substituent such as an alkyl group, a compound having two or more unsaturated bonds such as norbornadiene, and a compound having three or more ring structures, two of which form a norbornene skeleton. Examples of norbornene-based monomers having three or more ring structures include tricyclo[$5.2.1.0^{2,6}$]decene(dihydrodicyclopentadiene), a compound in which one or more molecules of cyclopentadiene are added to norbornene or dihydrodicyclopentadiene by Diels-Alder reaction (for example, tetracyclododecene, pentacyclopentadecene, hexacycloheptadecene, and the like), hydrogenated products thereof, isomers with different double bond positions, alkyl-substituted compounds, and the like.

Examples of norbornene-based monomers include bicyclo[2.2.1]-2-heptene (norbornene) and its derivatives. Examples of derivatives include a compound having a substituent such as an alkyl group, a compound having two or more unsaturated bonds such as norbornadiene, and a compound having three or more ring structures, two of which form a norbornene skeleton. Examples of norbornene-based monomers having three or more ring structures include tricyclo[$5.2.1.0^{2,6}$]decene(dihydrodicyclopentadiene), a compound in which one or more molecules of cyclopentadiene are added to norbornene or dihydrodicyclopentadiene by Diels-Alder reaction (for example, tetracyclododecene, pentacyclopentadecene, hexacycloheptadecene, and the like), hydrogenated products thereof, isomers with different double bond positions, alkyl-substituted compounds, and the like.

The sealant layer 43 may be a single film composed of one layer or a multilayer film composed of two or more layers. Furthermore, the sealant layer 43 has one or more layers formed of a cyclic olefin resin as a main component, and the cyclic olefin resin layer may be disposed to be the innermost side of the laminate 4, or may be disposed at a position near the interlayer. When the layer having a cyclic olefin resin as a main component is disposed on a sealing surface, it is possible to obtain the package 1 having the best non-adsorption performance. Furthermore, for example, in a case where the layer forming the sealing surface is polyethylene and the cyclic olefin resin layer is disposed as a layer outside the layer forming the sealing surface, a heat sealing time can be shortened. The time can be appropriately selected according to properties of the content 16.

In the present embodiment, a glass transition temperature of the material forming the sealant layer 43 is preferably 50° C. to 170°, and more preferably 70° C. to 140° C. When a glass transition temperature of the material forming the sealant layer 43 is 65° C. or higher, the sealant layer 43 tends to have excellent non-adsorption properties with respect to the content 16. Furthermore, when a glass transition temperature of the material forming the sealant layer 43 is 140° C. or lower, high temperature is not required at the time of laminating the laminate 4, and therefore moldability is excellent.

In the present embodiment, a thickness of the sealant layer 43 is preferably 20 µm or more and is more preferably 30 µm or more. When a thickness of the sealant layer 43 is 20 µm or more, a lamination process for the laminate 4 is facilitated, and sufficient seal strength can be obtained in a case where the sealant layers 43 are laminated to each other by heat sealing or the like to form the laminate 4 in a bag shape. In addition, a thickness of the sealant layer 43 is preferably 80 µm or less and is more preferably 60 µm or less. When a thickness of the sealant layer 43 is 80 µm or less, production cost can be reduced and appropriate flexibility can be imparted. The upper limit and the lower limit of a thickness of the sealant layer 43 can be arbitrarily combined.

It is known that, in a case where the sealant layer 43 contains a cyclic olefin resin, a water vapor permeation rate of the package 1 becomes lower as the sealant layer 43 becomes thicker. On the other hand, it has been found that as the sealant layer 43 becomes thicker, flexibility of the package 1 is lowered. Accordingly, the sealant layer 43 is preferably thick from the viewpoint of reducing a water vapor permeation rate of the package 1, but the sealant layer 43 is preferably thin from the viewpoint of ensuring flexibility of the bag main body 11.

In the present embodiment, the water vapor barrier layer 41 has a layer containing a fluorine resin as a forming material. Accordingly, the water vapor barrier layer 41 is more flexible than a case in which the water vapor barrier layer is a biaxially stretched polyester film which has been vapor-deposited with alumina or silica. Therefore, when comparing packages having the same laminate area, the amount of the content 16 that can be accommodated can be increased, and a space can be saved. In addition, the load of a micropump that operates to remove the content 16 is reduced, and followability is favorable in a case where an administration rate is constant or an administration rate is changed by program control.

By using a fluorine resin for the water vapor barrier layer 41, a water vapor permeation rate is sufficiently lowered while maintaining flexibility required to deform the bag main body 11 as compared with the case in which a barrier material other than a fluorine resin is used. That is, it is possible to provide the package 1 having excellent barrier properties against water vapor. In addition, since the water vapor barrier layer 41 has sufficient water vapor barrier performance, the sealant layer 43 can be thinned. A portable medical pump device, in which it is necessary to dispose the container 30 for the content 16 in a limited space, has an advantage in that the size of the device can be easily reduced because a space for storing the content 16 can be expanded by thinning the laminate 4 forming the accommodation part 30.

Mouth Part Member

The mouth part member 21 has, for example, a tubular shape such as a cylindrical shape, and is bonded to the laminates 4 on both sides without any gap therebetween by adhesion or heat sealing in a state where its base end part is inserted into the opening part 12 of the bag main body 11. The size of the mouth part member 21 is not limited in the present invention, but as an example, when an outer diameter excluding a convex portion is 4 to 10 mm, a wall thickness is 0.5 to 3 mm, and a length is about 5 to 30 mm, it is suitable as a connection part with a pump device. Furthermore, the mouth part member 21 may have a shape suitable for assembly so that the package 1 constitutes a part of the replaceable cartridge, and a joint part with the laminate 4 does not have to be a curved surface.

After filling the mouth part member 21 with the content 16, a sealing body (not shown) for preventing leakage to the outside, preventing invasion of dust and bacteria from outside of the system, and maintaining the quality of the content 16 is attached and sealed. As the sealing body, an elastic body formed of rubber or elastomer as a material is mainly used. Furthermore, in order to prevent the sealing body from falling off due to the action of an external force, a procedure of attaching caps, disposing sealing materials, and the like as needed, thereby fixing the sealing body is also commonly performed.

A specific state, a shape, and the like of the content 16 contained in the package 1 of the present embodiment are not particularly limited. The content 16 may be, for example, a solid, a liquid, a gas, a powder, a granule, a mixture, a composition, a dispersion, or the like. The content 16 may be a liquid or an aqueous solution containing a drug. When the content 16 is accommodated in the package 1, an inert gas such as nitrogen or a liquid may be filled, and the content 16 may be filled to a full volume without forming voids as much as possible.

The accommodation part 30 of the bag main body 11 can accommodate any material such as liquid, powder, gas, or a mixture thereof as long as these can pass through the mouth part member 21, but the present embodiment is particularly suitable for liquid pharmaceutical products that are required to be continuously administered by small amounts. Examples of these kinds of pharmaceutical products include hormones, narcotics for relieving pain, anticancer drugs, antibiotics, and the like, and it is common to perform a method of injecting these drugs subcutaneously and epidurally and into blood vessels, muscle, various organs, and the like by a micropump. In this case, administration can be controlled by an electric circuit or a computer, and a small amount of administration or finely controlled administration according to conditions of a patient can be performed. After the content 16 containing the pharmaceutical product is filled into the accommodation part 30, an inside plug is fitted into the opening part of the mouth part member 21, and a cap or the like is attached and sealed as necessary, it is installed in a cartridge of a form in which a replacement operation and carrying are easy. The content 16 can be stored in a sterile state by sterilizing the pharmaceutical product as the content 16 by steam heating after sealing or aseptically filling it.

According to the above configuration, it is possible to provide the novel package 1 which has a low water vapor permeation rate and excellent non-adsorption properties, and is easily deformed as the content 16 is discharged.

Hereinbefore, the preferable embodiments of the present invention have been described with reference to the accompanying drawings, but the present invention is not limited to the above examples. The shapes, combinations, and the like of the constituent members shown in the above-described examples are merely examples, and various changes can be made based on design requirements and the like without departing from the spirit of the present invention.

EXAMPLE

Hereinafter, the present invention will be described with reference to examples, but the present invention is not limited to these examples.

Manufacture of Laminate

Test Examples 1 to 3/Test Examples 6 to 9

An adhesive that forms an interlayer was applied to a bonding surface of a water vapor barrier layer such that a solid content became an adhered amount of 3.5 g/m². This was bonded with a sealant layer using a dry lamination method, and thereby a three-layered laminate having the water vapor barrier layer, the interlayer, and the sealant layer in this order was manufactured. As the sealant layer, a co-extruded two-layered laminate in which polyethylene (PE) and cyclic olefin (COP) were disposed adjacent to each other was disposed on a side such that a COP surface was in contact with contents by a simultaneous multi-layer extrusion film formation method.

Using a laminate having a material and a thickness of each layer shown in Table 1, laminates of Test Examples 1 to 3 and Test Examples 6 to 9 were obtained. In Table 1, a numerical value in parentheses [ ] is a thickness of each layer.

In addition, separately from this manufacture, a cylindrical mouth part member which had an outer diameter of 5 mm, an inner diameter of 3 mm, and a length of 10 mm, and which was formed of COP, was obtained by an injection molding method.

Test Examples 4 and 5

In Test Examples 4 and 5, resins as raw materials for each of the layers shown in Table 1 were respectively and separately heated and melt-mixed, and simultaneous multi-layer film formation was performed to form a film using an extruder capable of simultaneous multilayer extrusion molding. Thereby a three-layered laminate having a water vapor barrier layer, an interlayer, and a sealant layer in this order was obtained. As a material used for the interlayer, a material obtained by mixing components at a mass ratio shown in parentheses ( ) of Table 2 was used.

Test Examples 10 to 13

In Test Examples 10 to 13, a co-extruded two-layered laminate, in which a water vapor barrier layer and an interlayer were not disposed and a thickness of a sealant layer was variously changed from 50 µm to 250 µm, was used as it was. A thickness and a material of each of the layers are also shown in Table 1.

Manufacture of Package

The two laminates obtained above were cut out to make a rectangle of 50 mm×30 mm for one laminate, and the cut portions were overlapped such that the sealant layers faced inward. Two long sides and one short side of periphery portions were heat-sealed such that both sides had a width of 5 mm, and thereby a bag main body was obtained. Subsequently, the mouth part member was sandwiched between the laminates on unsealed sides of the bag main body, and the laminates and the mouth part member were joined together to manufacture a package.

The following materials were used as raw materials for the water vapor barrier layer, the interlayer, and the sealant layer.

PCTFE1: Polychlorotrifluoroethylene film (manufactured by Honeywell, ACLAR (registered trademark))

PCTFE2: Polychlorotrifluoroethylene pellets (manufactured by Daikin Industries, Ltd., NEOFLON PCTFE (trademark), DF0050-C1)

$Al_2O$-PET: Alumina vapor-deposited biaxially oriented polyester (manufactured by Toppan Printing Co., Ltd., GL Film (trademark))

COP: Cycloolefin polymer ((manufactured by Zeon Corporation, ZEONOR (registered trademark) 1020R)

PE: Linear low-density polyethylene (specific gravity 0.930 g/cm³, manufactured by TOSOH CORPORATION, Nipolon-L (registered trademark))

Adhesive: Urethane-based two-liquid curing-type laminate adhesive (manufactured by Mitsui Chemicals, Inc., TAKELAC (registered trademark))

TABLE 1

| | Water vapor barrier layer | Interlayer | Sealant layer | |
|---|---|---|---|---|
| | | | First layer | Second layer |
| Test Example 1 | PCTFE1 [15 µm] | Adhesive | PE [30 µm] | COP [20 µm] |
| Test Example 2 | PCTFE1 [20 µm] | Adhesive | PE [30 µm] | COP [20 µm] |
| Test Example 3 | PCTFE1 [23 µm] | Adhesive | PE [30 µm] | COP [20 µm] |
| Test Example 4 | PCTFE2 [15 µm] | Co-extruded adhesive layer 1 [15 µm] | PE [15 µm] | COP [20 µm] |
| Test Example 5 | PCTFE2 [15 µm] | Co-extruded adhesive layer 2 [15 µm] | PE [15 µm] | COP [20 µm] |
| Test Example 6 | PCTFE1 [51 µm] | Adhesive | PE [30 µm] | COP [20 µm] |
| Test Example 7 | PCTFE1 [76 µm] | Adhesive | PE [30 µm] | COP [20 µm] |
| Test Example 8 | PCTFE1 [102 µm] | Adhesive | PE [30 µm] | COP [20 µm] |

TABLE 1-continued

| | Water vapor | | Sealant layer | |
|---|---|---|---|---|
| | barrier layer | Interlayer | First layer | Second layer |
| Test Example 9 | Al$_2$O$_3$-PET [12 μm] | Adhesive | PE [30 μm] | COP [20 μm] |
| Test Example 10 | None | None | PE [30 μm] | COP [20 μm] |
| Test Example 11 | None | None | PE [80 μm] | COP [20 μm] |
| Test Example 12 | None | None | PE [130 μm] | COP [20 μm] |
| Test Example 13 | None | None | PE [180 μm] | COP [20 μm] |

TABLE 2

| | First component | Second component | Third component |
|---|---|---|---|
| Co-extruded adhesive layer 1 | LLDPE (50) | Admer (50) | — |
| Co-extruded adhesive layer 2 | LLDPE (70) | Elastomer (30) | Epoxy component (1) |

As materials shown in Table 2, the following materials were used.

LLDPE: Linear low-density polyethylene (manufactured by Japan Polyethylene Corporation, Harmolex (registered trademark) NH745N)

Admer Maleic acid anhydride modified polyethylene (manufactured by Mitsui Chemicals, Inc., ADMER (registered trademark))

Elastomer: Styrene-ethylene-butylene-styrene block copolymer (manufactured by Kraton Corporation, KRATON G (styrene content: 13 mass %, specific gravity: 0.90 g/cm$^3$, MFR=22 g/10 min (230° C., 5 kgf))

Epoxy component: Epoxidized 1,2-polybutadiene (manufactured by ADEKA Corporation, specific gravity: 0.99 g/cm$^3$, average molecular weight: 1,000)

Experiment 1

The following tests were carried out on the packages of Test Examples 1 to 13.

Amount of Discharged Liquid and Amount of Residual Liquid

A cylindrical rubber stopper made of butyl rubber having a diameter of 3.2 mm and a height of 8 mm was fitted into the mouth part of the manufactured package, and thereafter, the weight of the empty bag was measured and recorded. The package was housed in a spacer composed of two plate materials disposed parallel at intervals of 6 mm. A 21-gauge metal needle was pierced through the rubber stopper at the mouth part, and the metal needle and a plastic syringe were connected via a metal tube in which a pressure gauge was branched such that a fluid pressure could be monitored. A plunger of the syringe was pulled, and the air in the package was sucked. Thereafter, the package was filled with distilled water in the syringe by an operation of pushing the plunger until a pressure gauge showed 25 kPa (where ±2 kPa was within an allowable range). After the filling operation was completed, the metal needle was taken out from the rubber stopper, the total weight was measured, and by calculating the difference between the total weight and the weight of the empty bag, a filled liquid amount was obtained.

Next, a 21-gauge metal needle was pierced through the rubber stopper at the mouth part, and an empty plastic syringe was connected. While keeping the inside of the package at a negative pressure by pulling the plunger of the syringe, the distilled water in the package was removed. Thereafter, the weight of the package after removing the syringe and metal needle was measured, and by calculating the difference between this weight and the weight of the empty bag, a residual liquid amount was obtained. Then, a discharged liquid amount was calculated from the difference between the filled liquid amount and the residual liquid amount. A liquid amount was calculated by assuming that a volume of 1 g of distilled water was 1 cm$^3$.

When a discharged liquid amount was 3 cm$^3$ or more, it was determined as "suitable," and when a discharged liquid amount was less than 3 cm$^3$, it was determined as "unsuitable."

Water Vapor Permeation Rate

A water vapor permeation rate of the package was determined according to a water vapor permeability test in <7.02> plastic pharmaceutical product container test method of the Japanese Pharmacopoeia, 17th Edition. Specifically, each sample of the test example was filled with distilled water by (filled liquid amount)—0.1 (cm$^3$). Change in weight before and after storage for 14 days at a temperature of 25±2° C. and a relative humidity of 60±5% was calculated in percent unit, and this value was defined as a water vapor permeation rate.

As a standard for a plastic water-based injection container, it is specified that the weight loss from an initial content amount is 0.20% or less, and determination as "suitable" or "unsuitable" was made based on the standard.

The results of each test are shown in Table 3. Table 3 also shows a V/S value represented by a rate of a filled liquid amount V to an area S of the bag main body.

TABLE 3

| | Filled liquid amount V (cm$^3$) | Liquid-contacting area S (cm$^2$) | Residual liquid amount (cm$^3$) | Discharged liquid amount (cm$^3$) | Water vapor permeation rate (%) | V/S (cm$^3$/cm$^2$) | Test results |
|---|---|---|---|---|---|---|---|
| Test Example 1 | 3.52 | 16 | 0.17 | 3.35 | 0.04 | 0.220 | Suitable |
| Test Example 2 | 3.38 | 16 | 0.23 | 3.15 | 0.03 | 0.211 | Suitable |

TABLE 3-continued

| | Filled liquid amount V (cm³) | Liquid-contacting area S (cm²) | Residual liquid amount (cm³) | Discharged liquid amount (cm³) | Water vapor permeation rate (%) | V/S (cm³/cm²) | Test results |
|---|---|---|---|---|---|---|---|
| Test Example 3 | 3.31 | 16 | 0.24 | 3.07 | 0.02 | 0.207 | Suitable |
| Test Example 4 | 3.68 | 16 | 0.11 | 3.57 | 0.04 | 0.230 | Suitable |
| Test Example 5 | 3.77 | 16 | 0.08 | 3.69 | 0.04 | 0.236 | Suitable |
| Test Example 6 | 2.85 | 16 | 0.42 | 2.43 | 0.01 | 0.178 | Unsuitable |
| Test Example 7 | 2.67 | 16 | 0.59 | 2.08 | <0.01 | 0.167 | Unsuitable |
| Test Example 8 | 1.96 | 16 | 0.66 | 1.30 | <0.01 | 0.123 | Unsuitable |
| Test Example 9 | 3.10 | 16 | 0.45 | 2.65 | 0.02 | 0.194 | Unsuitable |
| Test Example 10 | 3.71 | 16 | 0.21 | 3.50 | 0.25 | 0.232 | Unsuitable |
| Test Example 11 | 3.35 | 16 | 0.45 | 2.90 | 0.21 | 0.209 | Unsuitable |
| Test Example 12 | 2.93 | 16 | 0.58 | 2.35 | 0.18 | 0.183 | Unsuitable |
| Test Example 13 | 2.67 | 16 | 0.74 | 1.93 | 0.11 | 0.167 | Unsuitable |

As shown in Table 3, it became clear that, in the packages of Test Examples 1 to 5 to which the present invention was applied, a discharged liquid amount could be increased while preventing loss of moisture. This result shows that the packages of Test Examples 1 to 5 have a high level of water vapor barrier properties and can accommodate a large amount of liquid in a small space. In addition, the package formed by the laminate obtained by the co-extrusion film formation method could be filled with a larger amount of liquid as a filled liquid amount, and in this package, a residual liquid amount after discharge tended to be small as compared to the package formed by the dry laminate.

Experiment 2

The package of Test Example 1 was filled with distilled water while controlling the amount of distilled water from 0.5 to 3.5 (cm³) in increments of 1 (cm³). A water vapor permeation rate and a V/S value were obtained by the same method as in Experiment 1, and the results are summarized and shown in Table 4.

TABLE 4

| | Filled liquid amount V (cm³) | Liquid-contacting area S (cm²) | Water vapor permeation rate (%) | V/S (cm³/cm²) | Test results |
|---|---|---|---|---|---|
| Test Example 1A | 3.50 | 16 | 0.04 | 0.219 | Suitable |
| Test Example 1B | 2.50 | 16 | 0.07 | 0.156 | Suitable |
| Test Example 1C | 1.50 | 16 | 0.15 | 0.094 | Suitable |
| Test Example 1D | 0.50 | 16 | 0.47 | 0.031 | Unsuitable |

Experiment 3

A package was formed by the same procedure as Experiment 1 except that a length of the long side of the bag main body was shortened from 5 (cm) to 3.5 (cm) in increments of 0.5 (cm) for the laminate of Test Example 1. (0.5 cm³) of distilled water was filled as a content, and a water vapor permeation rate and a V/S value were obtained by the same method as in Experiment 1 and Experiment 2. The results are summarized and shown in Table 5.

TABLE 5

|  | Filled liquid amount V (cm³) | Liquid-contacting area S (cm²) | Water vapor permeation rate (%) | V/S (cm³/cm²) | Test results |
|---|---|---|---|---|---|
| Test Example 1D | 0.50 | 16 | 0.47 | 0.031 | Unsuitable |
| Test Example 1E | 0.50 | 14 | 0.32 | 0.036 | Unsuitable |
| Test Example 1F | 0.50 | 12 | 0.26 | 0.042 | Unsuitable |
| Test Example 1G | 0.50 | 10 | 0.19 | 0.050 | Suitable |

When the amount of contents to be filled into the package of the same size is reduced, a numerical value represented by V/S becomes smaller. In addition, when a liquid-contacting area of the package which comes into contact with the liquid content is reduced for the same amount of contents, a numerical value represented by V/S becomes large. In the case of using the package of Test Example 1, when V/S is excessively reduced, a water vapor permeation rate is deviated from the standard. The reason for this is because an area of the laminate in which water vapor permeation occurs does not change even when a filled liquid amount is decreased. Furthermore, this is also not preferable from the viewpoint of occupying a large space in the pump device. When the amount of liquid to be filled is small, the amount of water permeation can be suppressed by reducing an area of the bag main body, and thereby storage suitability of contents can be secured.

On the other hand, when the package is designed such that V/S is large, it is advantageous from the viewpoint of a water vapor permeation rate, but when filling is continued beyond a certain volume, a peripheral edge seal portion is folded. In a case where a cyclic olefin resin is disposed in the sealant layer to impart storage suitability of contents, folding of the peripheral edge seal portion may cause cracking of the cyclic olefin resin, and therefore it is desirable that a V/S value not become large.

In addition, when a value of V/S is excessively large, pressure inside the package increases, and in a case where a continuous administration device or the like is connected to a mouth part to discharge contents, discharge of contents is likely to occur to eliminate bulging of a bag main body. Therefore, it becomes difficult to control an administration amount of liquid, or there may be load and damage to a micropump. Accordingly, it is desirable to design a package such that a V/S value is within a certain range to maintain an appropriate performance as a package. A V/S value is preferably within a range of 0.01 to 0.5, and more preferably 0.05 to 0.25.

REFERENCE SIGNS LIST

1 Package
11 Bag main body
11a Face
12 Opening part
15 Seal part
16 Content
21 Mouth part member
30 Accommodation part
30a Space after discharge
4 Laminate
41 Water vapor barrier layer
42 Interlayer
43 Sealant layer

What is claimed is:

1. A package, comprising:
a bag main body having an inner surface;
at least one mouth part member joined to the bag main body; and
a liquid content accommodated in the bag main body,
wherein the bag main body of the package has, as a forming material, a laminate consisting essentially of:
a water vapor barrier layer made of polychlorotrifluoroethylene;
a sealant layer comprising a polyethylene layer and a cyclic olefin resin layer disposed adjacent to each other, wherein the cyclic olefin resin layer is disposed to be the innermost side of the laminate; and
an interlayer positioned between the water vapor barrier layer and the sealant layer,
wherein the laminate is formed into a bag shape by bonding sealant layers facing each other,
the mouth part member is joined to the bag main body by being sandwiched between the sealant layers facing each other,
a thickness of the water vapor barrier layer is within a range of 15 μm to 25 μm,
a thickness of the sealant layer is within a range of 30 μm to 60 μm,
a volume V of the content accommodated inside the bag main body is 0.1 to 20 (cm³),
a relationship between an area S (cm²) of the bag main body which comes into contact with the liquid content accommodated inside the bag main body and the volume V (cm³) satisfies (Formula I):

$$0.05 \leq V/S \leq 0.25, \quad \text{(Formula I)}$$

wherein the area S is a total area of the inner surface of the bag main body.

2. The package according to claim 1, wherein
a volume of the bag main body is configured to be reduced according to the discharge of the content accommodated in the package through the mouth part member of the package.

3. The package according to claim 1, wherein a water vapor permeation rate of the package is 0.02% to 0.19%.

4. The package according to claim 1, wherein the total thickness of the laminate is within a range of 15 μm to 200 μm.

5. The package according to claim 1, wherein the mouth part member contains a cyclic olefin resin as a forming material.

6. The package according to claim 1, wherein the content is a pharmaceutical product.

7. The package according to claim 6, wherein the pharmaceutical product is a medical fluid.

8. The package according to claim 7, wherein the medical fluid contains one or more selected from hormones, medical narcotics, local anesthetics, analgesics, anticancer drugs, and antibiotics as components.

* * * * *